(12) United States Patent
Chan et al.

(10) Patent No.: US 8,835,453 B2
(45) Date of Patent: Sep. 16, 2014

(54) SUSTAINED RELEASE IMPLANT FOR GRANISETRON

(75) Inventors: Paonien Chan, Taipei County (TW); Shou-Chung Chao, Taipei County (TW); Shu-Chien Liu, Taipei County (TW); Fan-Jung Liu, Taipei County (TW); Li-Ya Wang, Taipei County (TW)

(73) Assignee: Development Center for Biotechnology, Taipei County (TW)

( * ) Notice: Subject to any disclaimer, the term of this patent is extended or adjusted under 35 U.S.C. 154(b) by 846 days.

(21) Appl. No.: 12/426,721

(22) Filed: Apr. 20, 2009

(65) Prior Publication Data

US 2010/0152226 A1 Jun. 17, 2010

(30) Foreign Application Priority Data

Dec. 11, 2008 (TW) ................................. 97148151 A

(51) Int. Cl.
*A61K 31/439* (2006.01)
*A61K 9/00* (2006.01)

(52) U.S. Cl.
CPC ............. *A61K 31/439* (2013.01); *A61K 9/0024* (2013.01)
USPC ........................................................ 514/299

(58) Field of Classification Search
CPC ........................... A61K 31/439; A61K 9/0024
See application file for complete search history.

(56) References Cited

U.S. PATENT DOCUMENTS

| | | | |
|---|---|---|---|
| 7,153,520 B2 * | 12/2006 | Seo et al. | 424/426 |
| 2005/0042194 A1 | 2/2005 | Ng et al. | |
| 2007/0264319 A1 | 11/2007 | Lebo et al. | |
| 2007/0265329 A1 * | 11/2007 | Devang et al. | 514/419 |

FOREIGN PATENT DOCUMENTS

WO  WO 2007069070  6/2007

OTHER PUBLICATIONS

Avgoustakis et al. In Journal of Controlled Release 79 (2002) pp. 123-135.*
Ramchandani et al. in Journal of Controlled Release 54, (1998) 167-175.*
Duvvuri et al. in Journal of Controlled Release 108, (2005) 282-293.*
'Granisetron Hydrochloride' at www.scbt.com/datasheet-203984-granisetron-hydrochloride.htmlsection (retrieved from the Internet Jun. 24, 2014).*
Office Action from counterpart Taiwan application 097148151 dated Dec. 1, 2011.
Avgoustakis, K. et al., PLGA-mPEG nanoparticles of cisplatin; in vitro nanoparticle degradation, in vitro drug release and in vivo drug residence in blood properties, Journal of Controlled Release, 2002, 123-135, 79.

* cited by examiner

*Primary Examiner* — Dennis Heyer
(74) *Attorney, Agent, or Firm* — WPAT, P.C.; Anthony King

(57) ABSTRACT

The main goals of the invention are to develop the long-term release of Granisetron injection implant composition with biodegradable polymer and to develop relative processing. Granisetron is mixed with different biodegradable polymers, and then hot melt extrusion technique with different diameter, temperature, rate of extrusion and holding time is applied to make implant. In vitro dissolution of the Granisetron injection implant composition shows the component continued release of the drug for over 7 days.

12 Claims, 10 Drawing Sheets

SUSTAINED RELEASE IMPLANT FOR GRANISETRON

FIELD OF THE INVENTION

Present invention relates to a pharmaceutical composition, especially to the pharmaceutical composition applying high molecular weight polymer for sustained drug release.

DESCRIPTION OF PRIOR ART

US Patent Publication No. 2005/0042194 reveals a semi-solid delivery vehicle containing a polyorthoester and an excipient. Semi-solid pharmaceutical composition comprises an active agent (such as Granisetron) and the delivery vehicle. The pharmaceutical composition may be a syringable or injectable formulation, and suitable for local delivery of the active agent. However, polyorthoester is a newly invented polymer. It still needs full pre-clinical and clinical safety evaluation prior to human medical use.

WO Patent Publication No. 2007/069070 reveals a pharmaceutical composition of aseptically filled multidose injectable dosage forms of Granisetron. It is used to prevent, reduce, and relieve acute and delayed nausea of patients treated with anti-tumor radioisotope therapy and chemotherapy. The pharmaceutical composition comprises Granisetron, preservatives and buffer of pH 4-6.

US Patent Publication No. 2007/0264319 reveals a Granisetron transdermal antiemesis delivery system which provides controlled release of Granisetron from the skin-contacting adhesive formulation of a transdermal patch, and maintains a sustained transdermal delivery of Granisetron. However, the antiemetic transdermal patch may cause allergy and other side effects.

US Patent Publication No. 2007/0265329 reveals a controlled release pharmaceutical composition of Granisetron in an injectable form for prevention, reduction and relief of acute and delayed nausea and vomiting induced by chemotherapy. Pharmaceutical composition comprises Granisetron, semi-solid delivery vehicle and pharmaceutically acceptable solution. It is using the same polyorthoester delivery vehicle as previously described US Patent Publication No. 2005/0042194, which still needs full pre-clinical and clinical safety evaluation before human medical use.

Developing an easy, effective, and equipped with controlled release and slow release of Granisetron sustained anti-nausea delivery system is something chemotherapy patients want and need to avoid nausea and vomit. Present invention provides such function in a sustained implant delivery system.

SUMMARY OF THE INVENTION

The present invention provides a pharmaceutical composition of sustained release implant comprising: (a) Granisetron base or a pharmaceutically acceptable salt thereof, and (b) biodegradable polymer, comprising poly(lactic-co-glycolic acid) (PLGA) and poly(lactic-co-glycolic acid)-polyethylene glycol (PLGA-PEG) in a weight ratio of 7.5:1 to 5:3, wherein the weight ratio of (a) and (b) is between 1:1 to 2:5.

The present invention also provides a method for preparation of Granisetron base or a pharmaceutically acceptable salt thereof sustained release implant comprising: (a) providing a mixture with biodegradable polymer and Granisetron; (b) filling the mixture into a hot mold of a hot melt extruder for hot melt, and (c) extruding an injectable implant by the hot melt extruder.

DETAILED DESCRIPTION OF THE INVENTION

Figure 1:
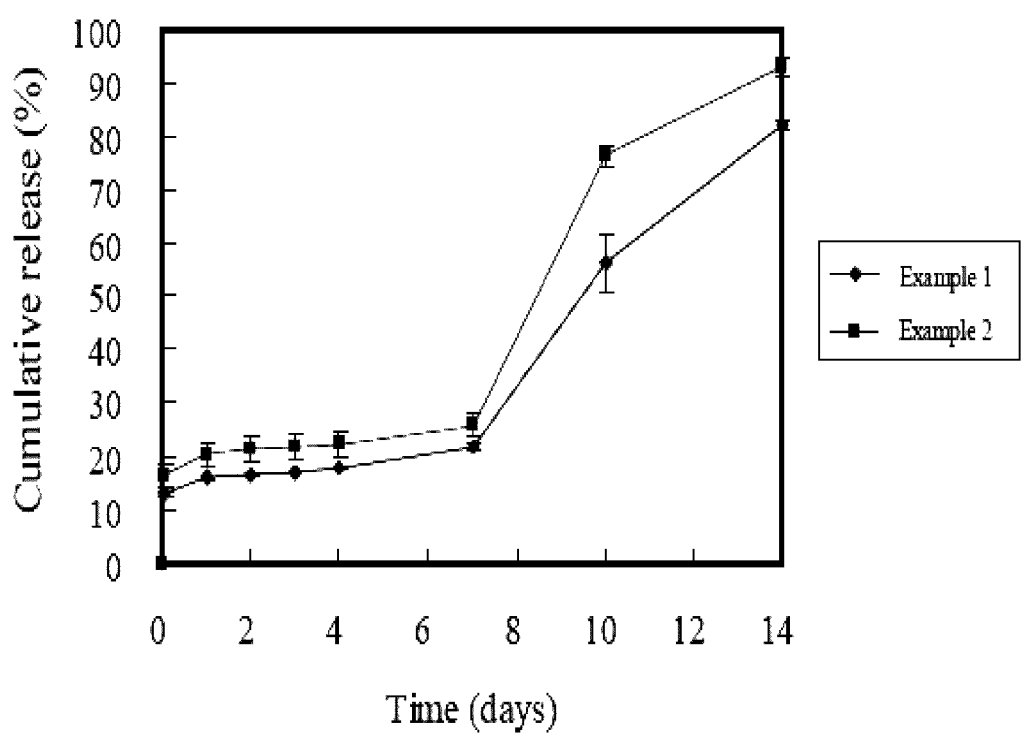
FIG. 1 shows dissolution profile of Examples 1 and 2.
Figure 2:
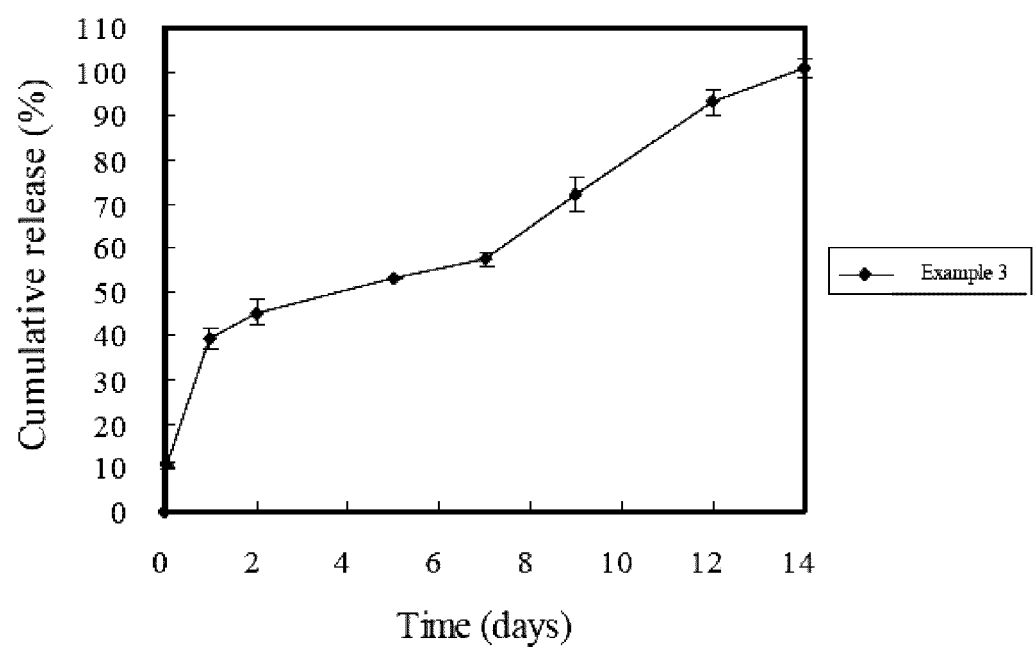
FIG. 2 shows dissolution profile of Example 3.
Figure 3:
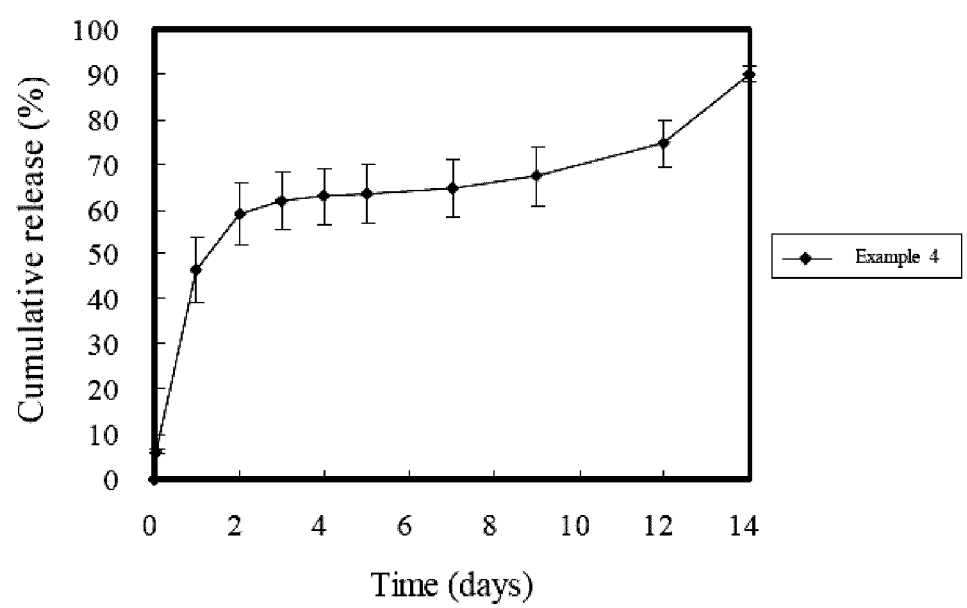
FIG. 3 shows dissolution profile of Example 4.
Figure 4:
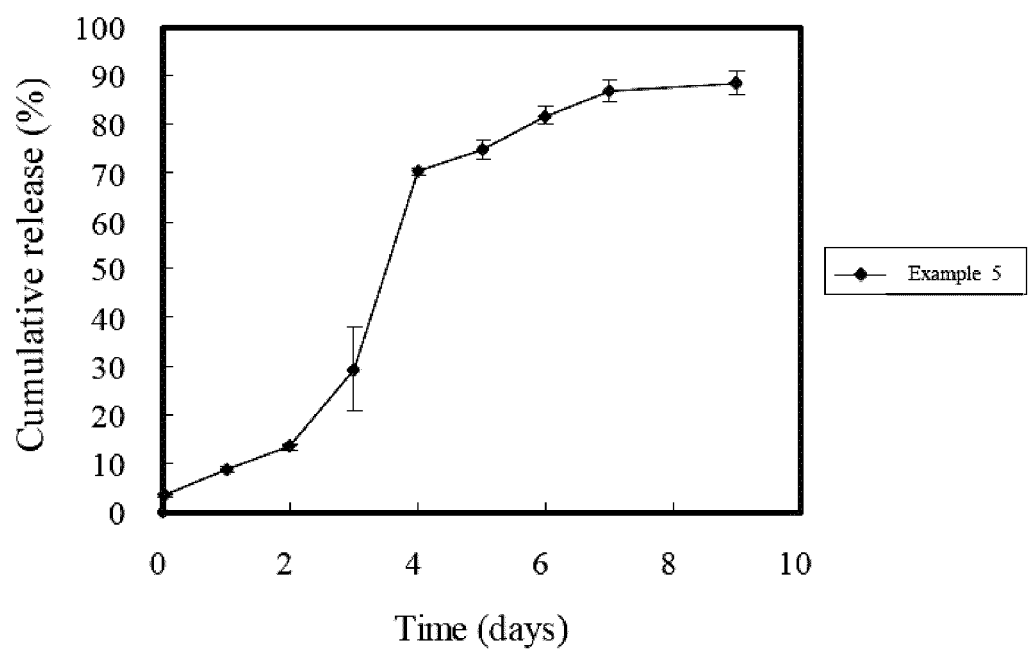
FIG. 4 shows dissolution profile of Example 5.
Figure 5:
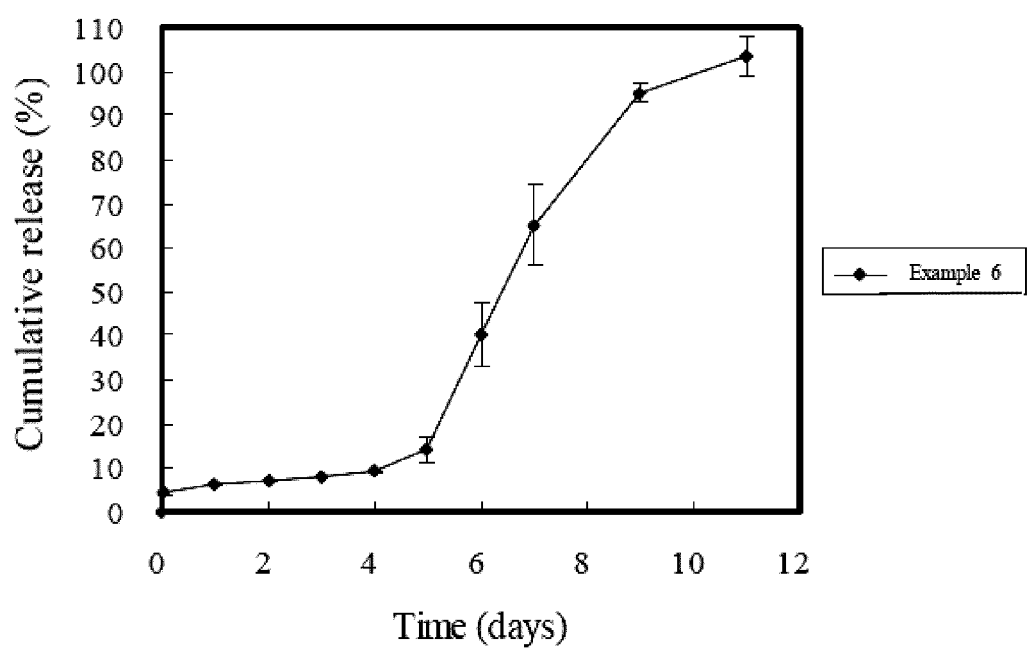
FIG. 5 shows dissolution profile of Example 6.
Figure 6:
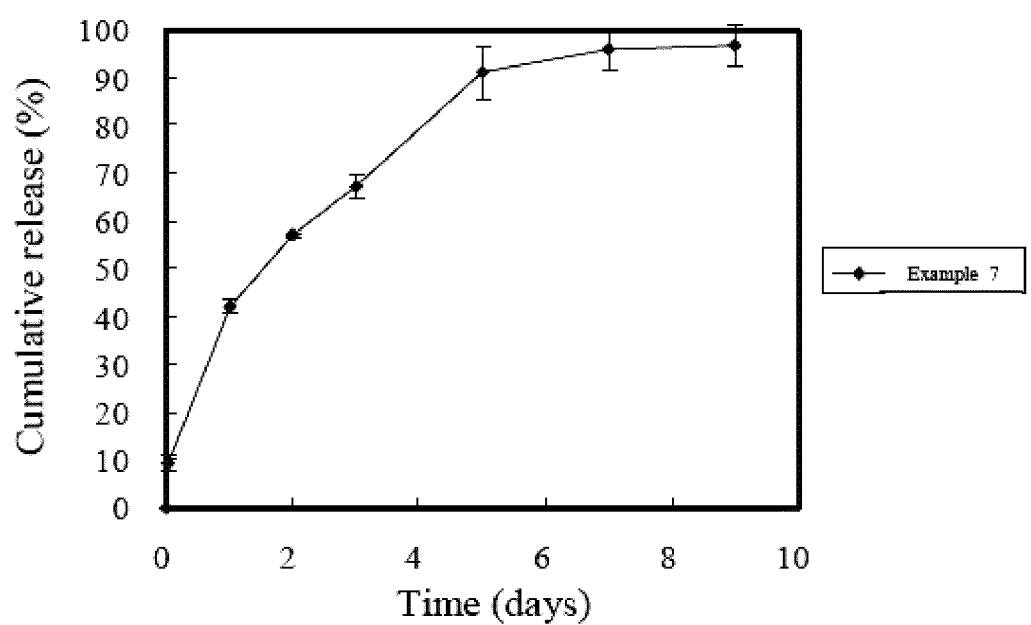
FIG. 6 shows dissolution profile of Example 7.

Cancer patient treated with traditional chemotherapy often has symptoms of nausea, vomiting, limb neurological paralysis, oral mucositis, and suppression of bone marrow blood forming mechanism. The most notorious side effect of all is nausea and vomiting. About 80% to 90% cancer patients suffer serious nausea and vomiting within 24 hours after chemotherapy. The vomiting caused by chemotherapy includes acute vomiting (within 24 hours after chemotherapy), delayed vomiting (after 24 hours of chemotherapy, may last 3 to 5 days), and expected vomiting (24 hours before next chemotherapy). Once developed nausea and vomiting, patients can't eat, and it further affects patient's nutrition status causing malnutrition, reducing immunity, and lowering patient's willingness to chemotherapy. Therefore, nausea and vomiting not only affect patient's life quality seriously, but also reduce patients' obedience or cause their inability to finish chemotherapy with appropriate dosage more importantly. It further leads to the increase of death rate, shortening living time, and seriously affecting treatment results of patients. Therefore, anti-vomiting agent is absolutely necessary for application when patients receive chemotherapy. Most current anti-vomiting agents on the market can relieve acute vomiting caused by chemotherapy, but are not effective to relieve delayed vomiting except Palonosetron (ALOXI®). ALOXI® can only work for medium level of delayed vomiting along with side effect of headache.

The present invention provides a pharmaceutical composition of controlled release Ganisetron implant, comprising 0.5 to 50 parts of poly(lactic-co-glycolic acid) (PLGA) and poly(lactic-co-glycolic acid)-polyethylene glycol (PLGA-PEG) mixture, based on 1 part of Granisetron. Preferred controlled release Granisetron implant pharmaceutical composition in the present invention comprises 1 to 10 parts of PLGA and PLGA-PEG mixture, based on 1 part of Granisetron. The implant formulation is a sustained release type. Current medicine using biodegradable polymer as pharmaceutical carrier on the market, such as ELIGARD®, ZOLADEX®, TRELSTAR®, and so on, provides drug release for more than a month. As for 3 to 5 days of delayed vomiting for chemotherapy patients, this invention provides drug release lasting for 7 days. It can continuously release drug without affecting next chemotherapy.

The chemical of Granisetron is endo-N-(9-methyl-9-azabicyclo[3.3.1]non-3-yl)-1-methyl-1H-indazole-3-carboxamide with molecular weight of 312.4. Known synthesis technique of Granisetron is listed in U.S. Pat. No. 4,884,808 in prior art as a reference of the present invention. Granisetron is therapeutically active in the free base form, as well as in pharmaceutically acceptable acid addition salts thereof. Granisetron hydrochloride, for example, is a white to off-white solid, having a molecular weight of 348.9, a reported melting point in the range of about 290 to about 292° C., and is soluble in water and normal saline at 20° C. Furthermore, the present invention extends to any pharmacological active ingredient, especially the pharmaceutical compounds with similar chemical characteristics of Granisetron. The term "granisetron," as used herein, includes the free base form of this compound, as well as pharmaceutically acceptable acid addition salts thereof. Granisetron hydrochloride is particularly preferred for the embodiments of the present invention.

Biodegradable polymer of the present invention indicates that lots of monomers polymerize to form material with huge molecular weight. The polymer is biocompatible, but hardly soluble or insoluble in water. It can be degraded by human body voluntarily, go through inner metabolism, and degraded molecules can be released to the outside. The carrier in the present invention for controlled drug release comprises but not limited to PLGA and PLGA-PEG. Ratio of lactic acid and glycolic acid of polymer is related to desired sustained release time. Selection range is from 100/0 to 40/60, and preferred range is from 100/0 to 50/50. For example, preparation of sustained release implant lasting more than 7 days comprises a ratio of lactic acid and glycolic acid of polymer as 50/50, wherein molecular weight of PLGA polymer Mn (number average molecular weight) ranges from 1900 to 17000 Mw (weight average molecular weight) ranges from 3500 to 32000 and that of PLGA-PEG polymer Mn ranges from 50000 to 70000 Mw ranges from 70000 to 120000. The ratio of PEG in PLGA-PEG is 5 to 20%, and preferred ratio is 5 to 15%.

The present invention further provides a preparation method of Granisetron sustained implant, comprising following steps:

1. Providing a Mixture with Biodegradable Polymer and Granisetron

In order to evenly distribute drug substance Granisetron in polymer evenly, a table-top crusher is used to crush polymer and Granisetron drug substance with medium speed, and sieve the powder through a mesh. Mix quantified amount of crushed polymer and Granisetron drug substance in Vortex Mixer for even distribution. The ratio of Granisetron and polymer is 1:1 to 2:5, and preferred ratio is 1:1 to 2:3. Preparation of various polymer mixture can be performed with table-top crusher with medium speed and sieve it through a mesh. Put quantified amount of polymer powder into Vortex Mixer to mix polymers and gain evenly distribute polymer mixture, or dissolve two polymer mixtures in dichloromethane and retain solid material after solvent evaporation. Dry solid material under vacuum condition, crush and sieve it to obtain well mixed micronized polymer.

2. Preparation of Injectable Implant Formulation

Injectable implant formulation is obtained by hot-melting extrusion process, including filling mixed Granisetron/polymer powder from step 1 into a hot mold of a hot-melt extruder and heating it at appropriate temperature. The temperature range is 50 to 110° C. (preferred temperature is 60 to 100° C.), heating time is 5 to 10 minutes (preferred time is 6 to 8 minutes), appropriate diameter of implant is 1.0 to 1.5 mm (preferred diameter is 1.0 to 1.35 mm) to obtain injectable implant formulation. Extrude the injectable implant by the hot melt extruder.

The examples below are non-limiting and are merely representative of various aspects and features of the present invention.

EXAMPLE

Example 1

Preparation of Granisetron HCl and PLGA in a Ratio of 2:3 for Controlled Release Injectable Implant Crushed PLGA polymer and Granisetron HCl active pharmaceutical ingredient with a crusher separately and passed it through no. 140 mesh (106 μm). 400 mg fine powder of Granisetron and 600 mg fine powder of PLGA polymer (weight average molecular weight of 12000) were mixed in Vortex Mixer for 2 minutes, and filled 1 g of PLGA polymer and Granisetron HCl mixture into a hot mold of a hot-melt extruder. The mixture material was heated in a mold chamber at 70° C. for 7 minutes to melt before extrusion. It generated injectable implant with diameter of 1.1 mm, and the injectable implant was stored in an air tight nitrogen-flushed container.

Example 2

The same experimental procedure was performed as shown in Example 1 by mixing Granisetron HCl and PLGA in a ratio of 2:3. While filling PLGA polymer and Granisetron HCl powder into the hot mold of the hot-melt extruder, heated it at 80° C. for 7 minutes to melt the mixture before extrusion. It generated injectable implant with diameter of 1.1 mm, and the injectable implant was stored in an air tight nitrogen-flushed container.

Example 3

The same experimental procedure was performed as shown in Example 1. Two polymers, PLGA (weight average molecular weight of 12000) and PLGA-PEG (weight average molecular weight of 80000), were mixed in a ratio of 5:1. Granisetron HCl and polymer mixture were mixed in a ratio of 2:3 and filled into the hot mold of the hot-melt extruder heated at 80° C. It generated injectable implant with diameter of 1.30 mm, and the dry injectable implant was stored in an air tight nitrogen-flushed container.

Example 4

The same experimental procedure was performed as shown in Example 1. Two polymers, PLGA (weight average molecular weight of 12000) and PLGA-PEG (weight average molecular weight of 80000), were mixed in the ration of 5:2. Granisetron HCl and polymer mixture were mixed in a ratio of 2:3 and filled into hot mold of hot-melt extruder heated at 80° C. It generated injectable implant with diameter of 1.35 mm, and the dry injectable implant was stored in an air tight nitrogen-flushed container.

Example 5

The same experimental procedure was performed as shown in Example 1. Granisetron HCl and polymer PLGA (weight average molecular weight of 6000) were mixed in a ratio of 2:3 and filled into the hot mold of the hot-melt extruder heated at 61° C. It generated injectable implant with diameter of 1.35 mm, and the dry injectable implant was stored in an air tight nitrogen-flushed container.

Example 6

The same experimental procedure was performed as shown in Example 1. Mixed one part of low molecular weight polymer PLGA (weight average molecular weight of 6000) and one part of high molecular weight polymer PLGA (weight average molecular weight of 12000) and dissolved them in dichloromethane. Solid substance after solvent evaporation and drying in vacuum was ground, and sieved to obtain homogeneous mixture of polymer microparticle. Granisetron and polymer mixture were mixed in a ratio of 2:3 and filled into the hot mold of the hot-melt extruder heated at 72° C. It generated injectable implant with diameter of 1.35 mm, and the dry injectable implant was stored in an air tight nitrogen-flushed container.

Example 7

The same experimental procedure was formed as shown in Example 6. Five parts of low molecular weight polymer PLGA (weight average molecular weight of 6000) and one part of high molecular weight polymer PLGA-PEG (weight average molecular weight of 80000) were mixed and dissolved them in dichloromethane. Solid substance after solvent evaporation and drying in vacuum was ground, and sieved to obtain homogeneous mixture of polymer microparticle. Granisetron and polymer mixture were mixed in a ratio of 1:1 and filled into the hot mold of the hot-melt extruder heated at 70° C. It generated injectable implant with diameter of 1.35 mm, and the dry injectable implant was stored in an air tight nitrogen-flushed container.

Example 8

The same experimental procedure was performed with same PLGA polymer mixture composition as shown in Example 7. Granisetron HCl and PLGA polymer mixture were mixed in a ratio of 40:60 and filled into the hot mold of the hot-melt extruder heated at 66° C. It generated injectable implant with diameter of 1.30 mm, and the dry injectable implant was stored in an air tight nitrogen-flushed container.

Example 9

The same experimental procedure with the same PLGA polymer mixture composition was performed as shown in Example 7. Granisetron HCl and PLGA polymer mixture were mixed in a ratio of 36:64 and filled into the hot mold of the hot-melt extruder heated at 74° C. It generated injectable implant with diameter of 1.35 mm, and the dry injectable implant was stored in an air tight nitrogen-flushed container.

Example 10

The same experimental procedure with the same PLGA polymer composition mixture was performed as shown in Example 7. Granisetron HCl and PLGA polymer mixture were mixed in a ratio of 38:62 and filled into the hot mold of the hot-melt extruder heated at 71° C. It generated injectable implant with diameter of 1.35 mm, and the dry injectable implant was stored in an air tight nitrogen-flushed container.

Example 11

The same experimental procedure was performed as shown in Example 1. Granisetron HCl and low molecular weight PLA (weight average molecular weight of 3500) were mixed in a ratio of 2:3 and filled into the hot mold of the hot-melt extruder heated at 100° C. It generated injectable implant with diameter of 1.3 mm, and the dry injectable implant was stored in an air tight nitrogen-flushed container.

Example 12

Figure 7:
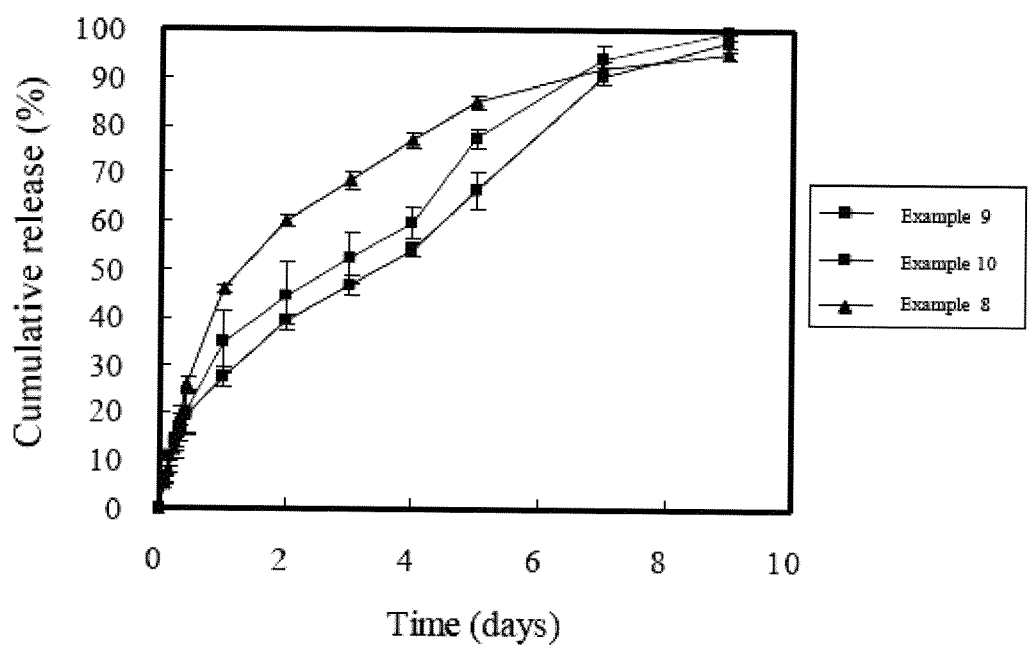
FIG. 7 shows dissolution profile of Examples 8 to 10.
Figure 8:
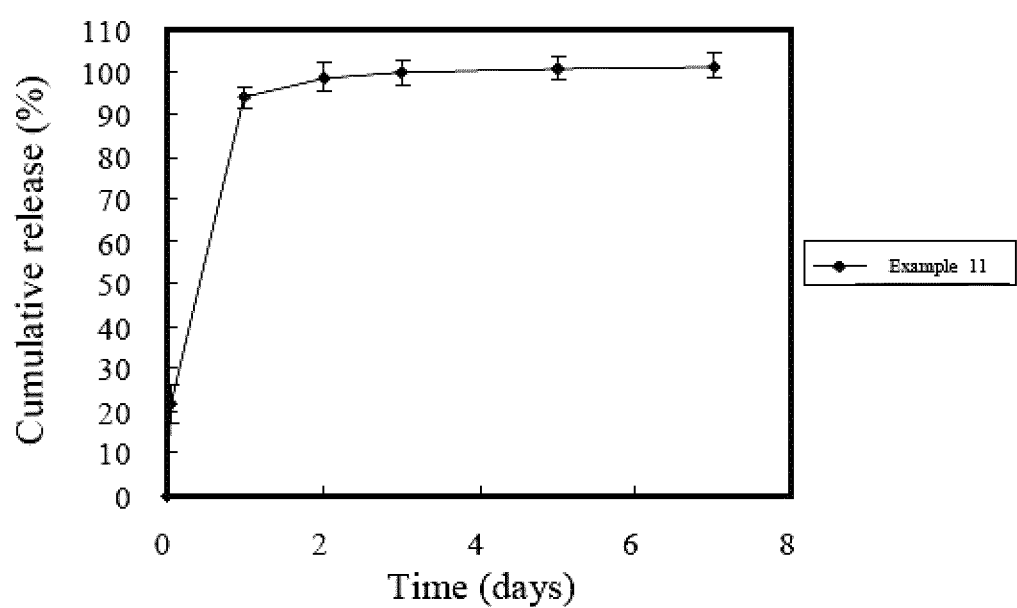
FIG. 8 shows dissolution profile of Example 11.

Dissolution test with Granisetron HCl implant obtained from Examples 1 to 11 was performed. Procedure was listed as follows: determined the weight of implant, put it into a screwed cap vial, and added 5 mL of pH7.4 isotonic PBS, and kept it in 37° C. water bath shaking at 50 rpm. Removed 1 mL solution after appropriate time, and used HPLC to analyze Granisetron HCl content. Removed residual solution from vials, added another flesh 5 mL of pH7.4 isotonic PBS, and continued the dissolution test. Medical dissolution profiles were shown in FIG. 1 to FIG. 8. Dissolution profile of FIG. 7 clearly showed that the sustained implant from the present invention can release Granisetron HCl for more than 7 days. According to the result of present invention, one shot of Granisetron sustained implant was enough for one-week dosage for anti-nausea.

Example 13

Figure 9:
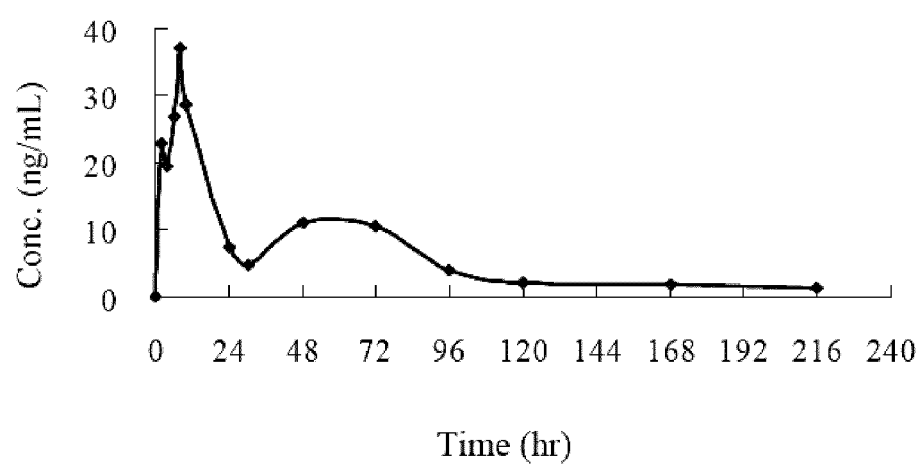
FIG. 9 shows drug concentration in animal serum of Example 10.
Figure 10:
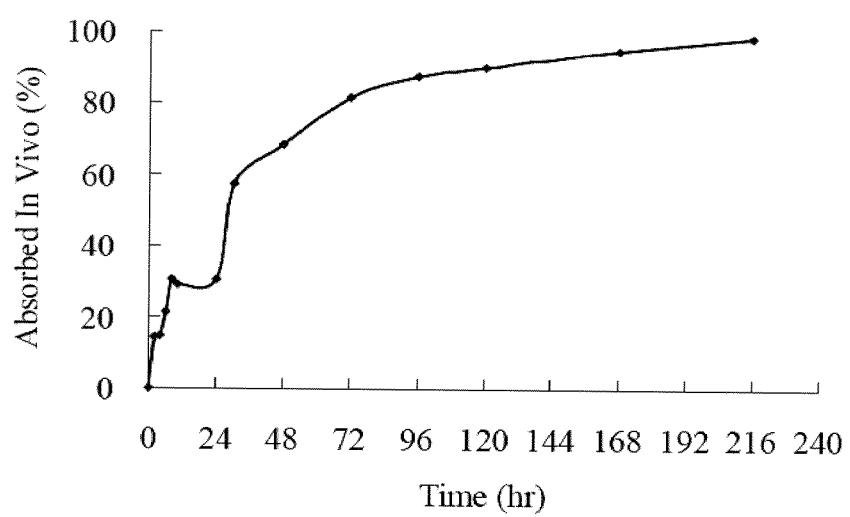
FIG. 10 shows absorption rate in vivo of Example 10.

In vivo animal test with Granisetron implant obtained from Example 10 was performed. Procedure was listed as follows. Male New Zealand White Rabbit was used as test animal with weight range of 3.0 to 3.5 Kg in triplicate. Granisetron HCl implant obtained from Example 10 in a dose of 10 mg/dose was injected to rabbits by subcutaneous route. 2 mL of blood from marginal ear vein after 2, 4, 6, 8, 10, 24, 30, 48, 72, 96, 120, 168, 216 hours of injection was taken. Supernatant was removed after centrifugation, and samples was extracted with toluene, and analyzed by HPLC. The blood concentration was calculated by WinNonlin (Scientific Consulting, Inc.) for plasma concentration-time area under curve (AUC) and absorption rate. Medicine concentration profile was shown in FIG. 9. Absorption rate was shown in FIG. 10. From results of FIGS. 9 and 10, it showed that sustained implant of present invention can last for more than 7 days of Granisetron HCl concentration in plasma.

Examples provided above are non-exclusive. Present invention and other variable points are obvious to people skilled in this art and are expected to be included in the scope of claim. The scope of current invention is based on claims, not limited in the examples above.

What is claimed is:

1. A solid implant sustained release pharmaceutical composition comprising:
   a pharmaceutically acceptable salt of Granisetron, and
   a mixture of biodegradable polymers, said mixture comprising poly(lactic-co-glycolic acid) (PLGA) and poly(lactic-co-glycolic acid)-polyethylene glycol (PLGA-PEG) in a weight ratio of 7.5:1 to 5:3,
   wherein the weight ratio of (a) and (b) is between 1:1 to 2:5.

2. The composition of claim 1, wherein the PLGA of biodegradable polymer comprising lactic acid and glycolic acid in a ratio of 1:1.

3. The composition of claim 1, wherein the PLGA-PEG of biodegradable polymer contains 5% to 15% of PEG.

4. The composition of claim 1, wherein the biodegradable polymer is from 1900 to 70000 number molecular weight (Mn), and the biodegradable polymer is from 3500 to 120000 weight average molecular weight (Mw).

5. The composition of claim 1, wherein the composition is sustained for 7-day drug release through subcutaneous injection.

6. The composition of claim 1, PLGA-PEG polymer is from 50000 to 70000 Mn, and PLGA-PEG polymer is from 70000 to 120000 Mw.

7. The implant of sustained release pharmaceutical solid composition of claim 1, PLGA-PEG polymer is from 50000 to 70000 Mn, and PLGA-PEG polymer is from 70000 to 120000 Mw.

8. A method of preparation of the composition according to claim 1 comprising:
   providing a mixture with biodegradable polymers and a pharmaceutically acceptable salt of Granisetron thereof;
   filling the mixture into a hot mold of a hot melt extruder for hot melt, and
   extruding an injectable implant by the hot melt extruder.

9. The method of claim 8, wherein temperature for the hot melt is from 60° C. to 100° C.

10. The method of claim 8, wherein diameter of the injectable implant is from 1.1 mm to 1.35 mm.

11. The method of claim 8, wherein the PLGA-PEG of biodegradable polymer contains 5% to 15% of PEG.

12. The composition of claim 1, wherein PLGA polymer is from 1900 to 17000 Mn, and PLGA polymer is from 3500 to 32000 Mw.

\* \* \* \* \*